(12) United States Patent
Frühauf et al.

(10) Patent No.: US 12,117,314 B2
(45) Date of Patent: Oct. 15, 2024

(54) SENSOR FASTENING FOR SINGLE-USE CONTAINERS

(71) Applicant: Endress+Hauser SE+Co. KG, Maulburg (DE)

(72) Inventors: Dietmar Frühauf, Lörrach (DE); Andreas Krumbholz, Maulburg (DE); Ralf Leisinger, Wieslet (DE)

(73) Assignee: Endress+Hauser SE+Co. KG, Maulburg (DE)

( * ) Notice: Subject to any disclaimer, the term of this patent is extended or adjusted under 35 U.S.C. 154(b) by 95 days.

(21) Appl. No.: 17/906,821

(22) PCT Filed: Mar. 8, 2021

(86) PCT No.: PCT/EP2021/055736
§ 371 (c)(1),
(2) Date: Sep. 20, 2022

(87) PCT Pub. No.: WO2021/185609
PCT Pub. Date: Sep. 23, 2021

(65) Prior Publication Data
US 2023/0145032 A1    May 11, 2023

(30) Foreign Application Priority Data
Mar. 20, 2020    (DE) ............. 10 2020 107 763.7

(51) Int. Cl.
*G01D 11/30*    (2006.01)
(52) U.S. Cl.
CPC .................. *G01D 11/30* (2013.01)

(58) Field of Classification Search
CPC ................................................. G01D 11/30
See application file for complete search history.

(56) References Cited

U.S. PATENT DOCUMENTS

| | | | | |
|---|---|---|---|---|
| 6,123,686 A * | 9/2000 | Olsen | ............... | F04B 49/065 417/279 |
| 2005/0163667 A1 * | 7/2005 | Krause | ............... | B01L 3/505 422/400 |
| 2013/0303965 A1 * | 11/2013 | Rossi | ............... | A61M 1/3667 604/404 |
| 2017/0286638 A1 * | 10/2017 | Searle | ............... | G16H 40/63 |
| 2018/0179486 A1 * | 6/2018 | Fadell | ............... | C12M 23/46 |

FOREIGN PATENT DOCUMENTS

| | | | | |
|---|---|---|---|---|
| DE | 102010007559 A1 * | 8/2011 | ......... | C12M 41/02 |
| DE | 102015110893 B3 | 3/2016 | | |
| DE | 102015116355 A1 | 3/2017 | | |
| EP | 2829598 A2 | 1/2015 | | |
| EP | 2513287 B1 * | 10/2016 | ......... | C12M 23/14 |
| EP | 3553159 A1 | 10/2019 | | |
| WO | WO-2015094540 A1 * | 6/2015 | ....... | A61B 5/02055 |

* cited by examiner

*Primary Examiner* — Jamel E Williams
(74) *Attorney, Agent, or Firm* — Mark A. Logan; Endress+Hauser (USA) Holding, Inc.

(57) ABSTRACT

A device for detachably fastening a sensor for determining and/or monitoring at least one process variable of a medium to a single-use container, wherein there is a connection between the device and a wall of the single-use container, comprises a fastening unit for detachably fastening the sensor to the single-use container. Disclosed also is a single-use container having a device according to the invention.

10 Claims, 3 Drawing Sheets

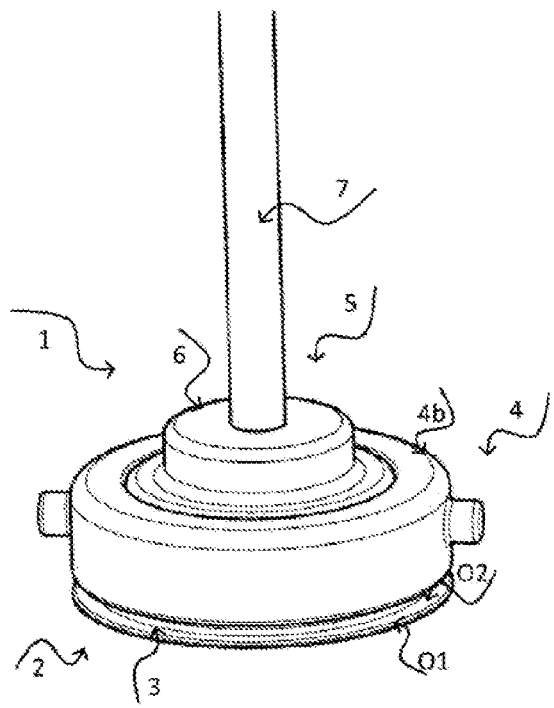
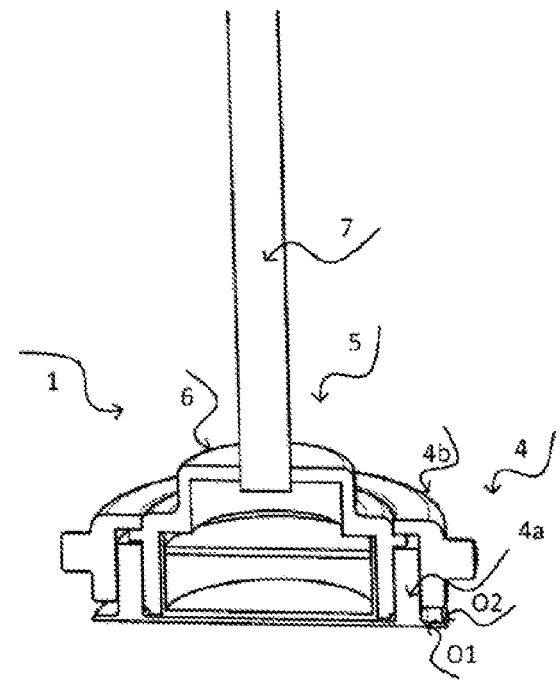
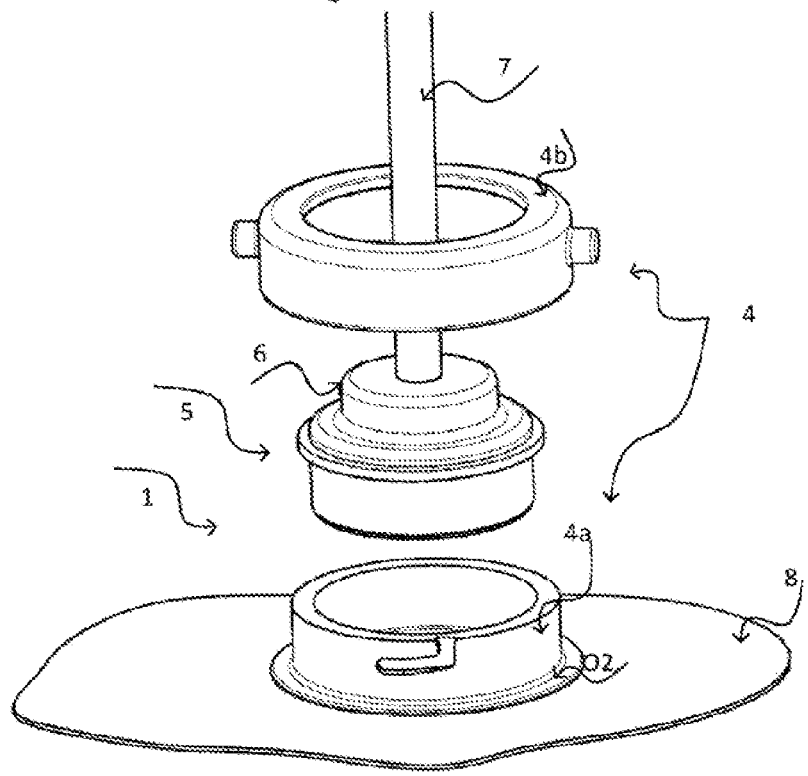
Fig. 3a
Fig. 3b
Fig. 3c

SENSOR FASTENING FOR SINGLE-USE CONTAINERS

CROSS-REFERENCE TO RELATED APPLICATIONS

The present application is related to and claims the priority benefit of DPMA Patent Application No. 10 2020 107 763.7, filed on Mar. 20, 2020, and International Patent Application No. PCT/EP2021/055736, filed on Mar. 8, 2021, the entire contents of which are incorporated herein by reference.

TECHNICAL FIELD

The present invention relates to a device for detachably fastening a sensor for determining and/or monitoring at least one process variable of a medium to a single-use container, and a single-use container having a device.

BACKGROUND

Many industrial processes, in particular pharmaceutical, biological, biochemical or biotechnological processes, are increasingly carried out using so-called single-use process solutions, for example in process plants with single-use technology. Such process plants include pipelines or reactors configured as single-use containers (disposable bioreactor or single-use bioreactor or single-use component). Such single-use containers can be, for example, flexible containers, for example bags, hoses or fermenters. Some single-use containers, for example bioreactors or fermenters, have feed and discharge lines which can be designed as hoses, or into which solid pipe sections can also be inserted as feed and discharge lines.

An advantage of single-use technology is that the single-use containers are disposed of at the end of each process. In this way, extensive cleaning and sterilization processes are avoided. In particular, the use of single-use containers prevents the risk of cross-contamination and thus increases process safety.

In order to monitor the processes carried out in single-use containers, a wide variety of physical and/or chemical process variables of the media contained in the single-use containers are recorded. In this case, a wide variety of sensors known per se from the prior art are used. For use in the field of single-use technology, however, the sensors have to fulfill various specific requirements.

On the one hand, many processes using single-use containers have to run without a connection to the environment, i.e. they form closed systems. It is thus customary to either introduce the sensors used into the single-use container (invasive sensors) or to fasten them to the single-use container from outside (non-invasive sensors). While the coupling to the medium is easier to accomplish in the case of invasive sensors, one advantage of non-invasive sensors is that they can in principle be used several times, i.e. for several single-use containers, and the requirements for sterility can be fulfilled much more easily.

In contrast, fastening the sensor to the single-use container is problematic in the case of non-invasive sensors. These flexible containers, which are generally made of a plastic, have only a low mechanical dimensional stability. Reproducible and detachable fastening is therefore not readily achievable.

SUMMARY

Therefore, the object underlying the present invention is to provide a reliable fastening option for non-invasive sensors for use with single-use containers.

With regard to the device, the object underlying the invention is achieved by a device for detachably fastening a sensor for determining and/or monitoring at least one process variable of a medium to a single-use container, wherein there is a connection between the device and a wall of the single-use container, and wherein the device comprises a fastening unit for detachably fastening the sensor to the single-use container.

Because the fastening unit enables the sensor to be detachably fastened to the single-use container, the sensor can be removed from the single-use container in a non-destructive manner. As a result, the sensor can be used several times. The device itself is connected to the wall of the single-use container.

In one embodiment, the device comprises a connection unit for producing the connection of the device to the wall of the single-use container. The connection unit serves, in particular, to ensure a reliable and reproducible connection to the single-use container. As a result, cavities in the region of a contact surface between the sensor and a wall of the single-use container can be avoided, for example.

In this regard, it is advantageous if the connection unit serves to ensure, in a contact region of the wall of the single-use container, an, in particular planar, integral connection. The connection unit is in particular designed such that no voids or cavities occur between the single-use container and the device. Preferably, the device is connected to the single-use container in a fully covering manner in the entire contact region.

It is also advantageous if the connection unit has a contact surface for producing the connection to the wall of the single-use container. The contact surface can be suitably adapted to the respective sensor and to the measurement principle used in each case. Adaptation to the geometry of the single-use container is also possible.

It is further advantageous if the connection unit has means for producing an adhesive bond, or vulcanization. The device is accordingly fastened to the single-use container by means of an adhesive bond or by means of vulcanization.

A further embodiment of the device provides that at least one component of the device can be produced together with the single-use container, in particular wherein the component and the single-use container can be integrally produced. In this case, subsequent modification of the single-use container in order to connect the device to the wall of the single-use container is not required.

A further embodiment provides that the fastening unit serves to produce a frictional and/or form-fitting connection between the sensor and the device. In this way, stable and robust fastening of the sensor to the single-use container can be ensured.

With regard to the fastening unit, it is advantageous if it has means for producing a click, latch, screw or bayonet connection, at least one guide rail or a snap hook.

It is further advantageous if the fastening unit has at least two fastening components. In this case, for example, a first fastening component may be associated with the device, while a second fastening component is associated with the sensor, in particular with a housing of the sensor. However, in other embodiments, both fastening components may also be associated with the device.

In the case of a screw connection, for example, the fastening unit can have a first fastening component in the form of a holder for the sensor with an external thread and a second fastening component, corresponding to the first, in the form of a union nut. In the case of a bayonet connection, however, the first fastening component can comprise a slot, while the second fastening component has a button for latching into the slot when a connection is produced between the two fastening components. Analogous considerations apply in the event that at least two fastening components are also provided for other fastening means.

A further embodiment provides that the connection unit comprises a flat base element, wherein a surface contour of a first surface of the base element is designed to correspond to the wall of the single-use container. In a further embodiment, the base element can be part of the connection unit.

It is advantageous if the connection between the device and the single-use container is at least partially produced in the region of the first surface of the base element. The first surface can have both a planar and an at least partially curved surface contour. Many different variants, for example a circular or rectangular cross-sectional area, are also conceivable with regard to the respective geometry. The fastening unit is in turn preferably arranged in the region of a second surface of the base element.

Due to the planar design, the wall of the container, which does not have a high dimensional stability, can be connected to the base element in a planar manner. The base element thus serves to avoid voids or cavities in the region of the connection.

With regard to the base element, it is advantageous if the base element is designed in the form of a flat plate. It is also advantageous if the base element has a through-opening in which the sensor is arranged when the sensor is fastened to the device. In this way, a component of the sensor, in particular a component of a sensor unit of the sensor, can be arranged directly on the wall of the single-use container. Depending on the measurement principle used, this can lead to a significant increase in the achievable measurement sensitivity and measurement accuracy.

The object underlying the invention is further achieved by a single-use container having a device according to the invention according to at least one of the described embodiments.

It is noted that the embodiments described in connection with the device according to the invention can also be applied mutatis mutandis to the single-use container according to the invention, and vice versa.

In summary, the use of a device according to the invention or a single-use container according to the invention allows stable and reproducible fastening of non-invasive sensors to single-use containers. By means of the solution according to the invention, voids or cavities between the sensor and the single-use container and/or between the device and the single-use container can be avoided. In addition, the device is characterized in that an arrangement of a single-use container, a device according to the invention and a sensor can be implemented in a particularly space-saving manner, in particular in a stackable manner. High positioning accuracy of the sensor relative to the single-use container can also be ensured. Finally, the solution according to the invention offers the advantage that an easily standardizable option for fastening non-invasive sensors to single-use containers is provided, enabling the sensors to be easily interchanged for different processes or applications.

BRIEF DESCRIPTION OF THE DRAWINGS

The invention and its advantageous embodiments are explained in more detail with reference to the following figures: The following is shown:

FIG. 3 shows various views of a device according to the present disclosure with a fastening unit having means for producing a bayonet connection, and a connection unit with a circular base element.

DETAILED DESCRIPTION

In the figures, identical elements are provided with the same reference signs.

Figure 1A:
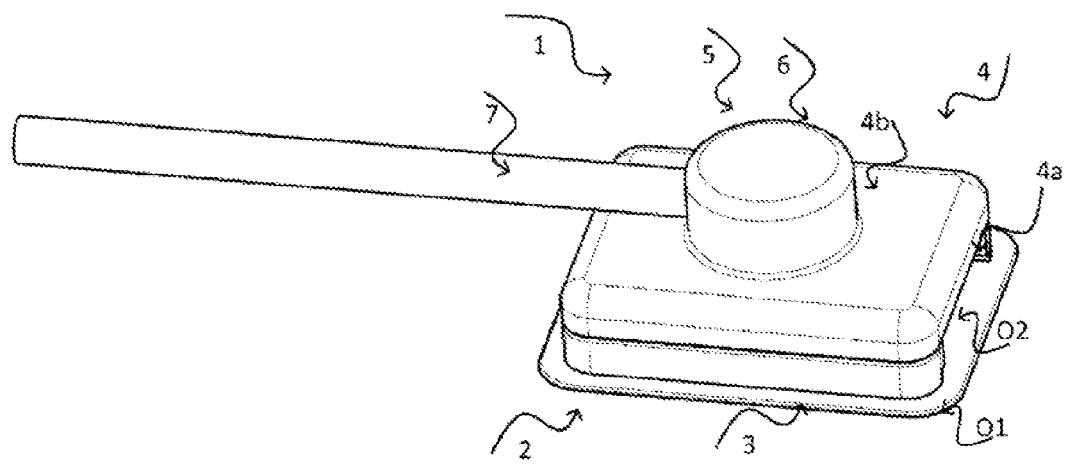
FIG. 1 shows various views of a device according to the present disclosure with a fastening unit having means for producing a latching connection, and a connection unit with a rectangular base element.
Figure 1B:
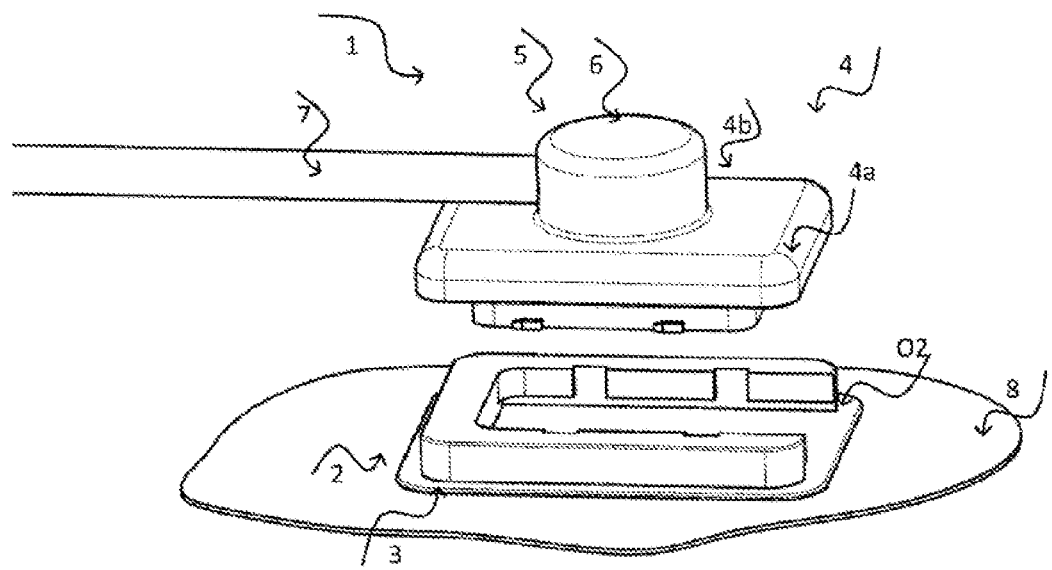
Figure 1C:
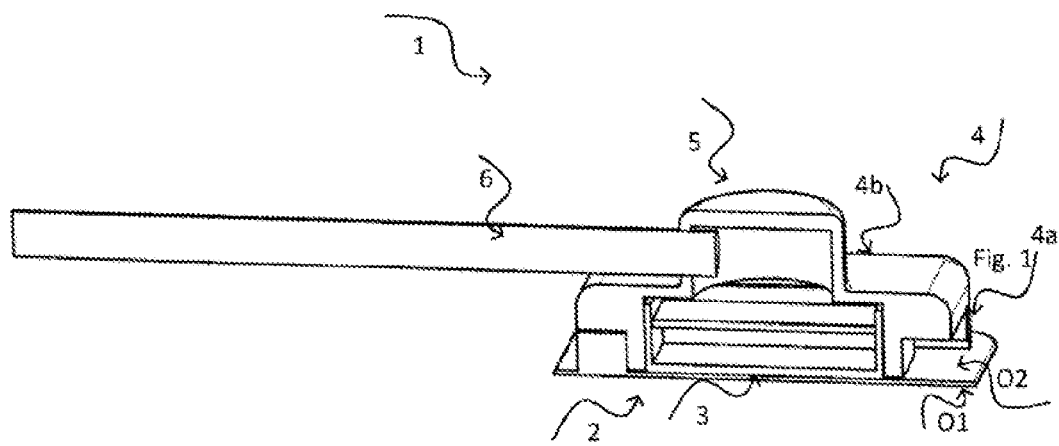

FIG. 1 shows three perspective views of a first embodiment of a device 1 according to the invention. The device 1 comprises a connection unit 2 for producing a connection between the device 1 and the single-use container 8, which connection unit 2 is designed in the embodiment shown a base element 3 in the form of a rectangular flat plate with rounded edges. However, numerous other geometries are also conceivable for the base element 3, which also fall within the scope of the present invention. For example, a surface of the base element 3 can be designed to be planar or at least partially curved, the geometry and size of the selected cross-sectional area is variable and the rounded edges are also only optional and are in no way absolutely necessary.

The connection to the single-use container 8 is made in the region of a first surface O1 of the base element 3, and can be achieved here by means of an adhesive bond. Alternatively, vulcanization can also take place, for example. The first surface O1 thus forms a contact surface of the connection unit 2.

The fastening unit 4 of the device 1 comprises two fastening components 4a and 4b. The first fastening component 4a is associated with the device 1 and is fixedly arranged on the second surface O2 of the base element. The second fastening component 4b is associated with a housing 6 of the sensor 5, which sensor 5 also has an electrical contact 7 in the form of a connecting cable. Other sensors 5 can also be designed without connecting cables 7. For the variant shown, the first fastening component 4a comprises a holder with two guide rails which have recesses for engaging latching hooks, which latching hooks in turn are part of the second fastening component 4b. However, numerous further variants for fastening the sensor 5 to the device 1 are conceivable, all of which fall within the scope of the present invention.

Figure 2:
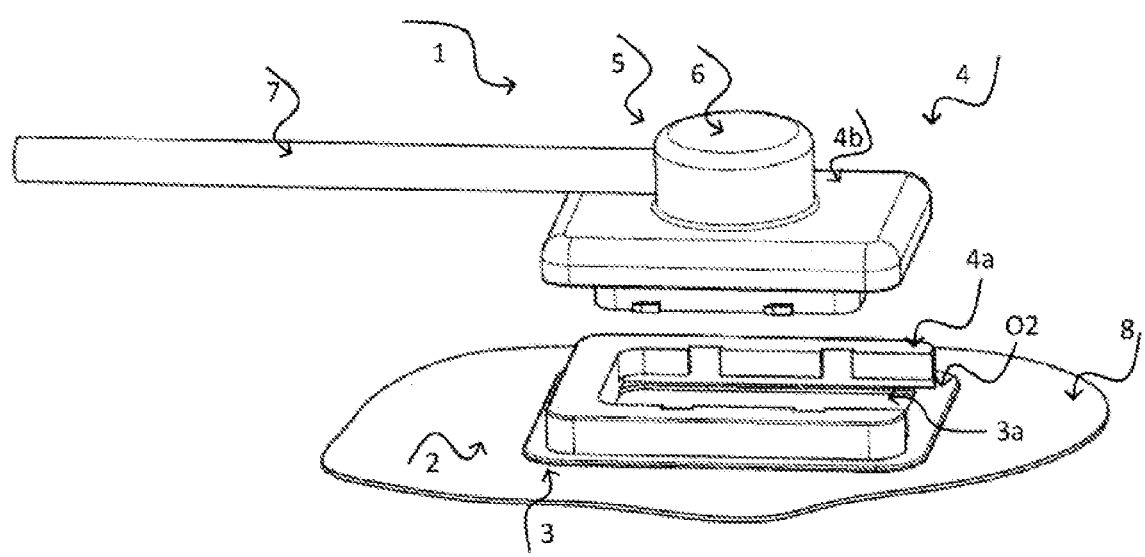
FIG. 2 shows a second embodiment of a device according to the present disclosure similar to FIG. 1, wherein the base element has a through-opening.

In contrast to FIG. 1, the base element 3 has a through-opening 3a for the embodiment of the device 1 according to FIG. 2. The base element 3 thus has the function of a frame for this embodiment. The sensor unit of the sensor 5 is thus directly in contact with the wall of the single-use container 8.

The illustration shown enables the device 1 and the sensor 5 to be arranged in a particularly flat manner on a single-use container 8, i.e. the device 1 and the sensor 5 together have a comparatively low height.

In the embodiment according to FIG. 3, the base element 3 is circular. As in the case of the previously shown embodiments, the fastening unit 4 comprises two fastening components 4a and 4b. In contrast to FIG. 1 and FIG. 2, the fastening unit 4 here comprises means for producing a bayonet connection. This allows precise axial arrangement of the sensor 5 relative to the device 1 and to the single-use container 8. The first fastening component 4a also has a holder. Two slots are introduced into the holder, and buttons of the second fastening component 4b latch into said slots when the second fastening component is connected to the first fastening component 4a, and which is configured in the form of a union nut.

The invention claimed is:

1. A device for detachably fastening a sensor for determining and/or monitoring at least one process variable of a medium to a single-use container, wherein there is a connection between the device and a wall of the single-use container, the device comprising:
   a fastening unit for detachably fastening the sensor to the single-use container; and
   a connection unit for producing the connection of the device to the wall of the single-use container,
   wherein the connection unit serves to ensure, in a contact region of the wall of the single-use container, an integral connection,
   wherein the connection unit has a contact surface for producing the connection to the wall of the single-use container.

2. The device according to claim 1,
   wherein at least one component of the device can be integrally produced together with the single-use container.

3. The device according to claim 1,
   wherein the fastening unit serves to produce a frictional and/or form-fitting connection between the sensor and the device.

4. The device according to claim 3,
   wherein the fastening unit has means for producing a click, latch, screw or bayonet connection, at least one guide rail or a snap hook.

5. The device according to claim 4,
   wherein the fastening unit has at least two fastening components.

6. A device for detachably fastening a sensor for determining and/or monitoring at least one process variable of a medium to a single-use container, wherein there is a connection between the device and a wall of the single-use container, the device comprising:
   a fastening unit for detachably fastening the sensor to the single-use container; and
   a connection unit for producing the connection of the device to the wall of the single-use container,
   wherein the connection unit has means for producing an adhesive bond, or vulcanization.

7. A single-use container, comprising:
   a device for detachably fastening a sensor to the single-use container, the device including:
      a fastening unit for detachably fastening the sensor to the single-use container, and
      a connection unit for producing the connection of the device to the wall of the single-use container,
      wherein the connection unit comprises a flat base element, wherein a surface contour of a first surface of the base element is designed to correspond to the wall of the single-use container,
   wherein the sensor is for determining and/or monitoring at least one process variable of a medium in the single-use container,
   wherein there is a connection between the device and a wall of the single-use container.

8. The single-user container according to claim 7,
   wherein the connection between the device and the single-use container is at least partially produced in the region of the first surface of the base element and/or wherein the fastening unit is arranged in the region of a second surface of the base element.

9. The single-user container according to claim 8,
   wherein the base element is designed in the form of a flat plate.

10. The single-user container according to claim 9,
   wherein the base element has a through-opening in which the sensor is arranged when the sensor is fastened to the device.

* * * * *